US007065175B2

(12) United States Patent
Green

(10) Patent No.: US 7,065,175 B2
(45) Date of Patent: Jun. 20, 2006

(54) X-RAY DIFFRACTION-BASED SCANNING SYSTEM

(75) Inventor: Michael C. Green, Palo Alto, CA (US)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 74 days.

(21) Appl. No.: 10/379,271

(22) Filed: Mar. 3, 2003

(65) Prior Publication Data

US 2004/0174959 A1 Sep. 9, 2004

(51) Int. Cl.
*G01N 23/04* (2006.01)
(52) U.S. Cl. .......................... 378/57; 378/70; 378/98.8
(58) Field of Classification Search .................. 378/19, 378/51, 53, 54, 57, 70, 86, 88, 98.8, 154, 378/155, 145–147; 250/370.08, 370.09, 250/370.11
See application file for complete search history.

(56) References Cited

U.S. PATENT DOCUMENTS

| 5,007,072 | A | * | 4/1991 | Jenkins et al. ................. 378/88 |
| 5,600,700 | A | | 2/1997 | Krug et al. ..................... 378/57 |
| 5,818,897 | A | * | 10/1998 | Gordon .......................... 378/19 |
| 6,041,097 | A | * | 3/2000 | Roos et al. ..................... 378/62 |
| 6,370,227 | B1 | * | 4/2002 | Guru et al. ................... 378/149 |
| 6,442,233 | B1 | | 8/2002 | Grodzins et al. ............... 378/57 |
| 6,470,071 | B1 | * | 10/2002 | Baertsch et al. ............... 378/62 |
| 2001/0033636 | A1 | | 10/2001 | Hartick et al. | |

FOREIGN PATENT DOCUMENTS

EP 0354045 2/1990

OTHER PUBLICATIONS

Michael C. Green, Larry D. Partain, "High throughput baggage scanning employing x-ray diffraction for accurate explosives detection", Proceedings of SPIE vol. 5048, presented Mar. 4, 2003, p. 63-72, Nondestructive Detection and Measurement for Homeland Security, Conference 5048, Mar. 4-5, 2003, Proceedings of SPIE vol. #5048, 4 pages.
Airport Report, American Association of Airport Executives, vol. XLVII, No. 12, Jun. 15, 2002, 14 pages.
R.A. Street, et al. "Comparison of $PbI_2$ and $HgI_2$ for direct detection active matrix x-ray image sensors", Journal of Applied Physics, vol. 91, No. 5, Mar. 1, 2002, p. 3345-3355.

(Continued)

*Primary Examiner*—Edward J. Glick
*Assistant Examiner*—Courtney Thomas
(74) *Attorney, Agent, or Firm*—Blakely, Sokoloff, Taylor & Zafman LLP

(57) ABSTRACT

An x-ray diffraction-based scanning method and system are described. The method includes screening for a particular substance in a container at a transportation center using a flat panel detector having a photoconductor x-ray conversion layer to detect x-rays diffracted by a particular substance in the container. The diffracted x-rays may be characterized in different ways, for examples, by wavelength dispersive diffraction and energy dispersive diffraction.

61 Claims, 14 Drawing Sheets

OTHER PUBLICATIONS

G. Harding, et al. "Energy-dispersive x-ray diffraction tomography", Phys. Med. Biol., 1990, vol. 35, No. 1, p. 33-41.

H. Bomsdorf, "Coherent X-ray scatter for non-destructive testing of works of art", Dec. 1999, vol. 4, No. 12, 8 pages.

H. Strecker, Automatic detection of explosives in airline baggage using elastic X-ray scatter, Medicamundi, vol. 42, Issue 2, Jul. 1998, p. 30-42.

XES 3000 Fully Automatic Explosives Detection System (EDS brochure), YXLON International, 2002.

Automatic Detection of Explosives in Airline Baggage Using Elastic X-Ray Scatter, H. Strecker, vol. 42, Issue 2, p. 30-33, Jul. 1998.

Comparison of $PbI_2$ and $HgI_2$ for Direct Detection Active Matrix X-Ray Image Sensors, R.A. Street et al., Journal of Applied Physics, vol. 91, No. 5, p. 3345-3355, Mar. 1, 2002.

* cited by examiner

X-RAY DIFFRACTION-BASED SCANNING SYSTEM

TECHNICAL FIELD

This invention pertains to the field of x-ray scanning systems and, in particular, to x-ray diffraction-based scanning systems.

BACKGROUND

The events of Sep. 11$^{th}$ 2001 forced recognition of an urgent need for more effective and stringent screening of airport baggage. The need for security expanded from the inspection of carry-on bags for knives and guns to the complete inspection of checked bags for a range of hazards with particular emphasis upon concealed explosives. The demonstrated willingness of terrorists to die in the pursuit of their aims meant that 100% passenger-to-bag matching, which could be put in place rapidly, was not sufficient to counter an attempt to conceal explosives in checked baggage and bring down an airliner. Successful screening for the presence of explosives presents numerous technological challenges, many of which are not met in present systems. X-ray imaging is the most widespread technology currently employed for screening. Last year approximately 1100 x-ray explosives detection systems incorporating computerized tomography (CT) scanners were purchased by the Transportation Security Agency (TSA) in an accelerated procurement program directed toward a goal of 100% screening of checked bags by Dec. 31$^{st}$ 2002.

Existing x-ray baggage scanners, including CT systems, designed for the detection of explosive and illegal substances are unable to discriminate between harmless materials in certain ranges of density and threat materials like plastic explosive. Thus, depending upon the level of the sensitivity setting, they either pass through a percentage of threat material, "missed detection" in security parlance, or they generate a high rate of false positives. CT scanner-based explosives detection systems are able to overcome problems of superimposition effects that arise in line scan systems. CT measures average x-ray absorption per voxel in slices projected through suspect regions of a bag. This parameter is not sufficiently specific to distinguish explosives from many other common materials. Items implicated in false positives include candy, various foodstuffs (e.g., cheese), plastics, and toys. Much attention has attended the deployment of CT-based explosives detection systems and their high false positive rate of around 30% in real world operating conditions is now well publicized in the media and has been acknowledged by the TSA. Concerns have been expressed about the resultant need to open and hand search a substantial portion of the checked bags, out of sight of the owner of the luggage. This is time consuming and expensive for the airlines and the prospect of airport delays and the potential for theft is a source of concern to the traveling public.

Moreover, CT scanners are unable to detect the presence of explosive material that is formed into thin sheets because CT averages the x-ray absorption coefficient over each voxel. Pentaerythritoltetranitrate (PETN), for example, will readily detonate when in the form of a sheet 1 mm thick. The density of PETN is 1.77 g/cc and a sheet 50 cm×50 cm×1 mm, easily incorporated into the skin of a suitcase, weighs approximately 442 grams, or almost 1 pound, which is sufficient to cause a powerful explosion.

Identification systems based on X-ray diffraction techniques provide enormously improved discrimination of materials. Such systems measure the d-spacings between the lattice planes of micro-crystals in materials. This form of energy-selective diffraction imaging has been employed in a type of medical tomography and in the non-destructive examination of pigments in works of art. X-ray diffraction provides a substance-specific fingerprint that greatly increases the probability of specific material detection and concomitantly reduces the incidence of false positives. Its applicability to explosives detection and the detection of other illicit substances has been demonstrated by Yxlon International of Germany with a prototype diffraction-based system.

Prior x-ray diffraction-based security systems for explosives detection and baggage scanning are not yet highly developed. These systems, such as Yxlon's system as illustrated in FIG. 1, are based upon work done by Bomsdorf and Muller at the University of Wuppertal in Germany. The Yxlon system utilizes small-area, single-crystal germanium (Ge) detectors. A divergent tight cluster of collimated x-ray pencil beams, originating from an effective point source, is directed through the bag under examination and sensed by the high-purity Ge detector cooled to liquid nitrogen temperature of −196 degrees C. However, such a system suffers from a number of fundamental constraints. First, the high-purity Ge detector is too expensive to use in large area sensors. Second, the requirement for liquid nitrogen cooling is cumbersome and expensive to maintain in an airport environment. In addition, they can examine only a small area of a bag at one time due to the small detector size. This requires multiple passes of the beam through the bag being screened in which the beam is meander-scanned (zig-zag, back-and-forth pattern) through the bag in order to inspect the entire contents of the bag. This is too slow for volume applications like routine baggage scanning. Tests done by the Canadian Customs on detecting concealed samples of heroin and cocaine, which for a diffraction system is an equivalent task to identifying an explosive compound, have indicated scan times of the order of 1.5 minutes, far longer than the desired 6 seconds per bag.

SUMMARY OF THE INVENTION

An x-ray diffraction-based scanning method and system are described. In one embodiment, the method includes providing a flat panel detector having a photoconducting x-ray conversion layer and screening for a particular substance in a container at a transportation center using the flat panel detector.

Other features and advantages of the present invention will be apparent from the accompanying drawings, and from the detailed description, which follows below.

BRIEF DESCRIPTION OF THE DRAWINGS

The present invention is illustrated by way of example and not intended to be limited by the figures of the accompanying drawings in which like references indicate similar elements and in which.

DETAILED DESCRIPTION

Figure 1:
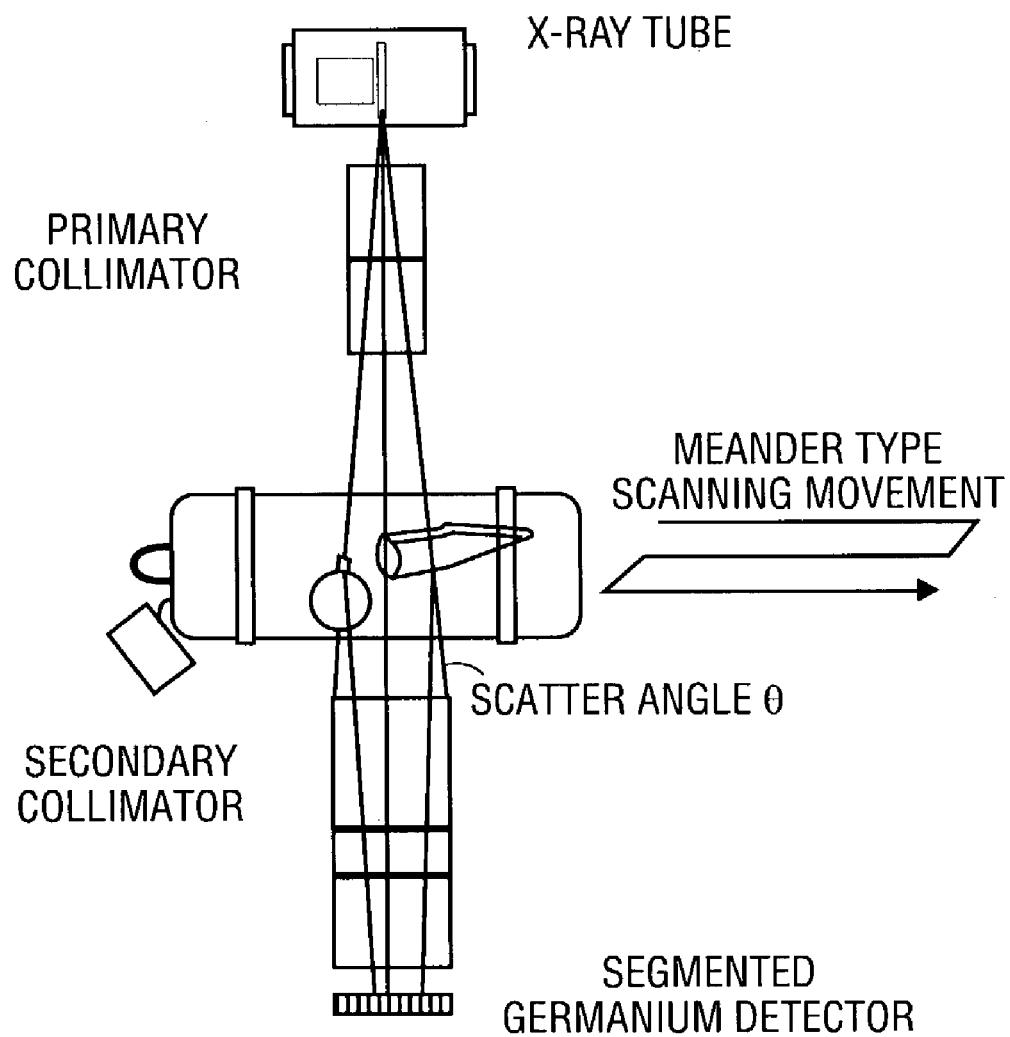
FIG. 1 illustrates a prior art x-ray diffraction scanning system.

In the following description, numerous specific details are set forth such as examples of specific components, processes, etc. in order to provide a thorough understanding of the present invention. It will be apparent, however, to one skilled in the art that these specific details need not be employed to practice the present invention. In other instances, well known components or methods have not been described in detail in order to avoid unnecessarily obscuring the present invention.

The terms "above," "below," and "between" as used herein refer to a relative position of one layer or component with respect to another. As such, one layer deposited or disposed above or below another layer, or between layers, may be directly in contact with the other layer(s) or may have one or more intervening layers. Moreover, one component in front, behind, below or between another component may be in physical contact with the other component or may have one or more intervening components, or may be otherwise indirectly coupled with other component. The term "coupled" as used herein means connected directly to or connected indirectly through one or more intervening components or operatively coupled through non-physical connection (e.g., optically).

A diffraction-based x-ray system is described. The diffraction-based x-ray system may be used to detect and measure atomic layer spacing in crystalline and microcrystalline materials to provide a means of specific material identification. Classical x-ray diffraction takes place from the atomic layer planes in crystals. In accordance with the Bragg equation, constructive interference takes place when:

$$N\lambda = 2d \sin \theta$$

where, $\lambda$ is the x-ray photon wavelength, d is the atomic layer plane spacing, and $\theta$ is the diffraction angle. The d-spacings of the atomic layer planes are substance-specific and diffraction data provides a non-contact x-ray fingerprint for identifying crystalline materials.

In one particular embodiment, the x-ray system may be used for transportation center (e.g., an airport, train station, etc.) container (e.g., bags, luggage, boxes, etc.) scanning for the detection of a particular substance, for example, an explosive. The majority of explosive compounds are well-crystallized solids at room temperature. Even "plastic explosive" is composed of a high explosive such as PETN or RDX in powder form, which is highly crystalline on a micro-scale, dispersed in a soft binder of polyurethane and wax.

The sensitivity of the diffraction technique is enhanced by the nature of the typical baggage contents, e.g., predominantly garments, paper and plastics, which are amorphous materials which do not interact with the incident x-ray beam to give strong coherent diffraction signals. Metals are crystalline (in particular, microcrystalline) and efficiently diffract x-rays, but the atomic layer d-spacings in the compact crystal lattices of metals are small, e.g., in the range 0.5–2.5 Angstroms (Å), compared to those of larger crystalline organic compounds which are typically in the range 2–10 Å. Therefore, x-ray diffraction lines that originate from metal materials are distinguishable from those from most other materials, including explosives.

The x-ray diffraction system may use conventional wavelength-dispersive (WD) diffraction or fixed-angle, multi-wavelength diffraction for improved throughput. In addition, the use of a large-area flat-panel x-ray detector having a two dimensional array of pixels, or multiple smaller area flat-panel detectors, coupled with an elongated x-ray source may permit a full three-dimensional (3D) volumetric x-ray diffraction scan of a container in a single pass and, thereby, improve the throughput of the screening system. Further, orthogonal collimators may placed in front of the flat panel detector to limit the acceptance angle of x-ray photons entering the flat panel detector and also ensure that each small block of pixels of the flat panel detector(s) views a separate area of the sheet beam, thereby dividing it into volume elements.

Although the diffraction-based x-ray system may be described at times in relation to the detection of explosives for baggage screening for ease of discussion, the system is not so limited. In alternative embodiments, the diffraction-based x-ray system described herein may be used to detect other substances and for other purposes.

Figure 2A:
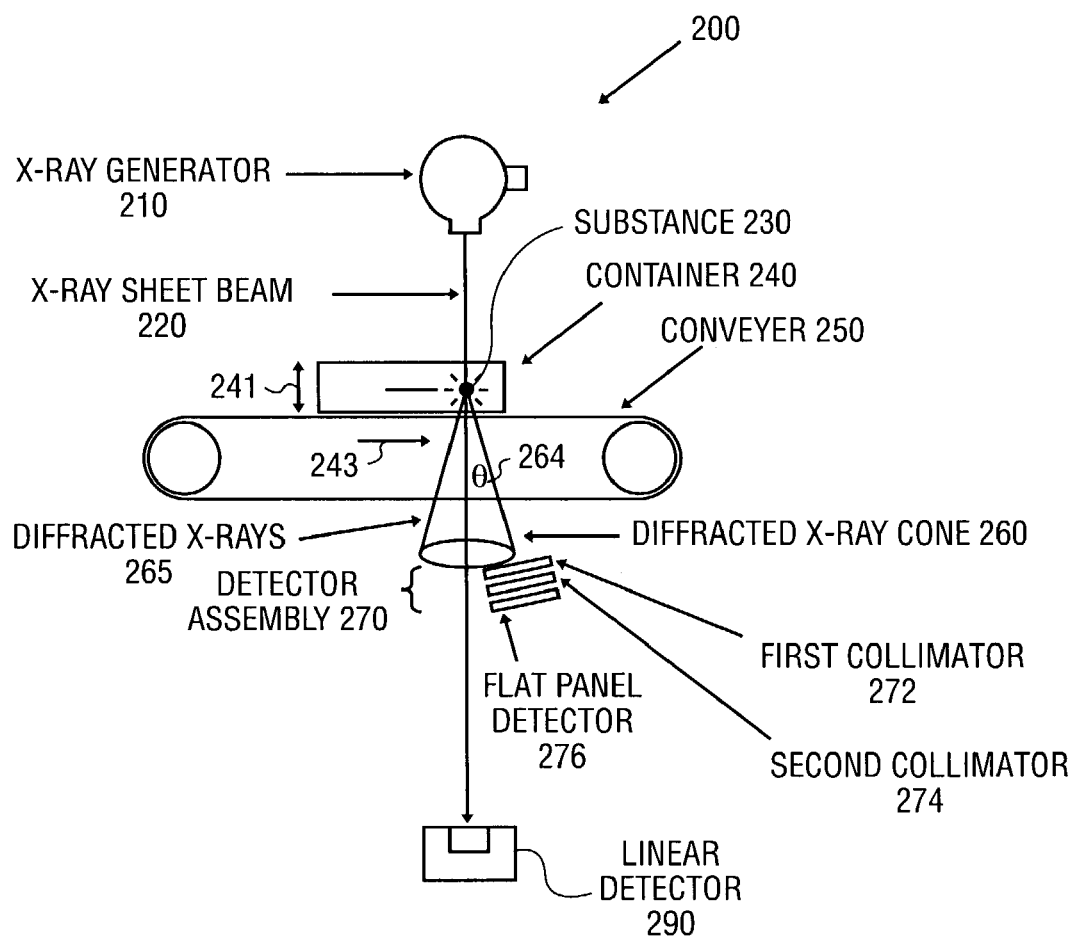
FIG. 2A is a cross-section view illustrating one embodiment of an x-ray diffraction system.
Figure 2B:
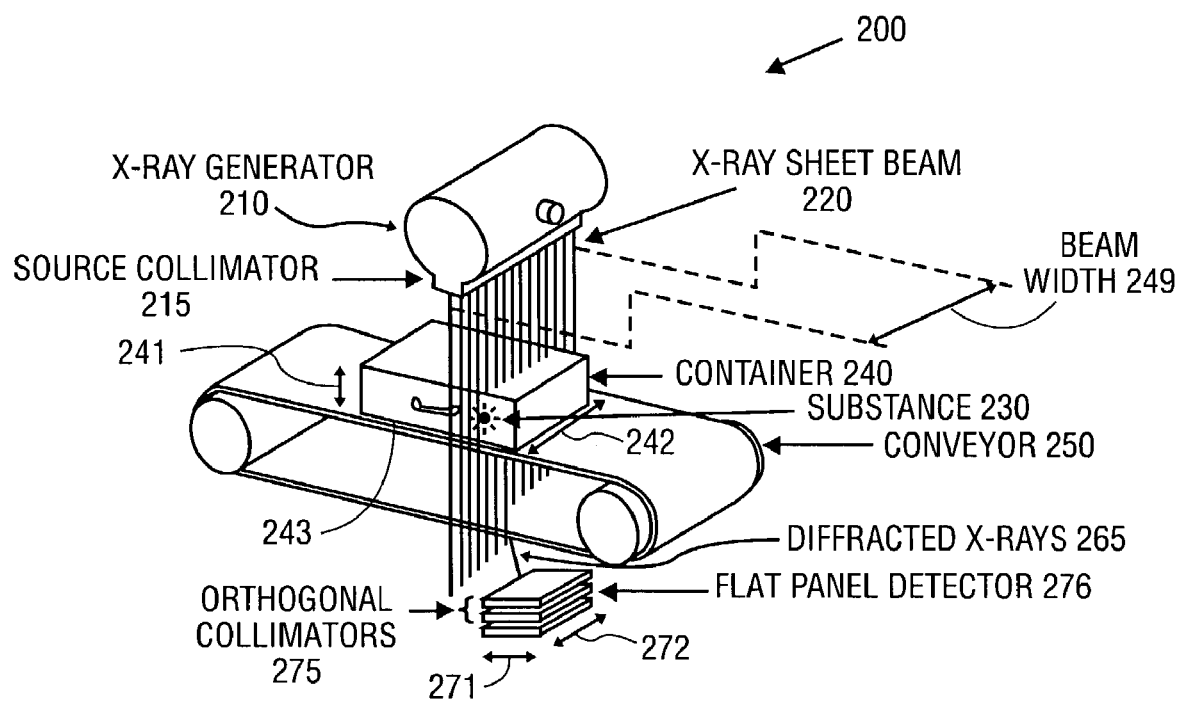
FIG. 2B is a perspective view, respectively, illustrating one embodiment of an x-ray diffraction system.

FIGS. 2A and 2B are a cross-section view and a perspective view, respectively, illustrating one embodiment of an x-ray diffraction system. The x-ray diffraction system 200 includes an x-ray generator 210 having an x-ray source, a pair of collimators 275, and a two dimensional (2D) flat panel detector (FPD) array 276. The x-ray generator 210 is composed of an x-ray tube with a longitudinally extended target and one or more x-ray beams to generate an x-ray sheet beam 220, as further illustrated in FIG. 8. In one embodiment, the x-ray sheet beam 220 is composed of a continuous highly collimated x-ray sheet. In an alternative embodiment, the x-ray sheet beam 220 is composed of multiple close parallel-collimated sub-beams generated by source collimator 215.

Figure 8:
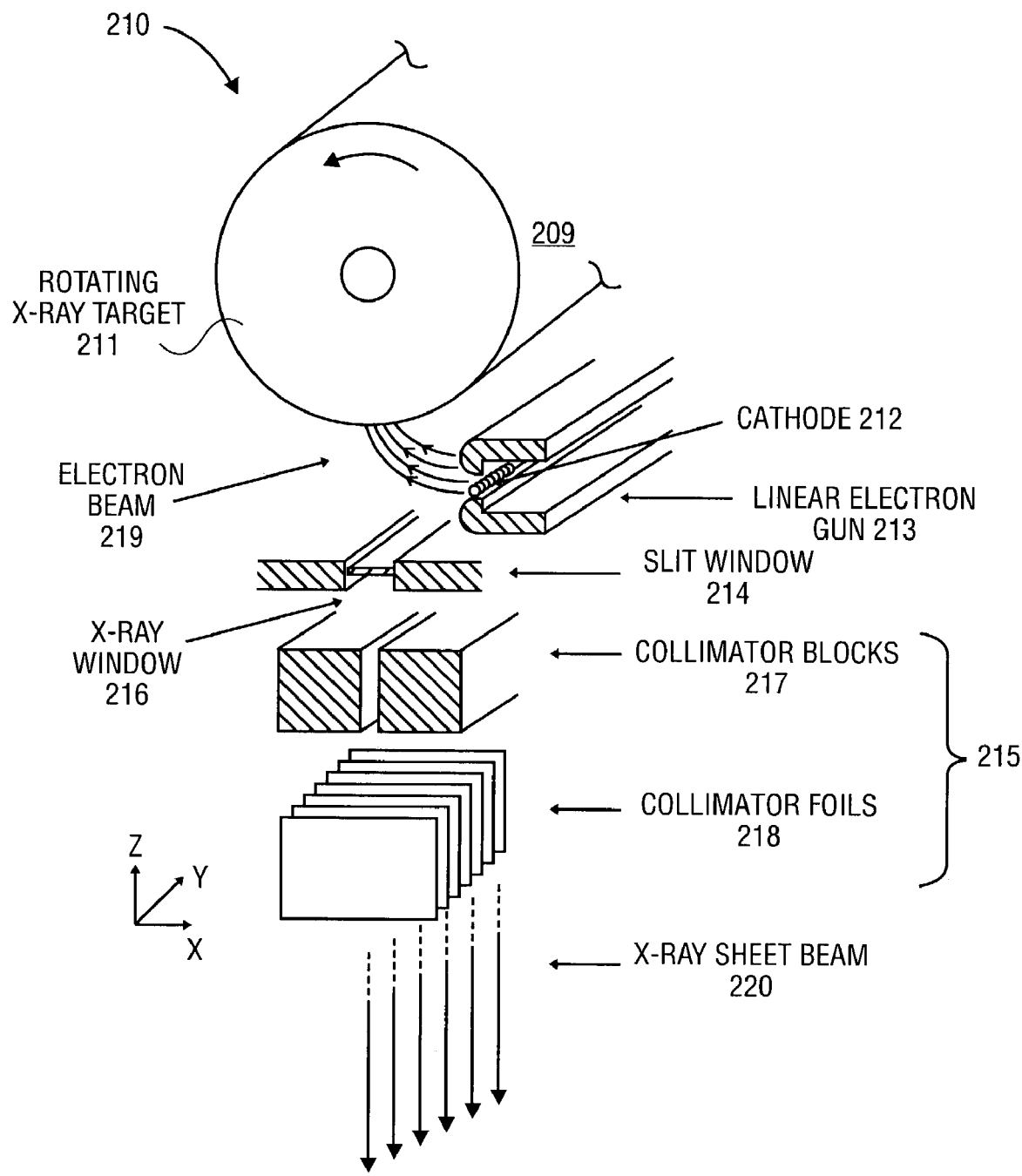
FIG. 8 illustrates one embodiment of an x-ray generator.

As illustrated by FIG. 8, source collimator 215 may include collimator blocks 217 that operate to limit beam divergence in the x-direction and collimator foils 218 that operate to limit beam divergence in the y-direction. A linear electron gun 213 may be used to generate an electron beam 219 using cathode 212. The electron beam 219 strikes the surface 209 of an elongated (e.g., in the range of 1 mm to 2 meters) rotating x-ray target (anode) 211 to generate x-rays that emanate through window 216. In one particular embodiment, target 211 has a width of approximately 1 meter. As discussed above, collimator 215 may be used to collimate the x-rays to produce x-ray sheet beam 220. The shape of the beam may be configured by altering the shape of x-ray target 211. In one embodiment, for example, cuts may be made in surface 209 to produce a "picket-fence-like" x-ray sheet beam 220 composed of multiple, individual beams. It should be noted that alternative configurations for the x-ray generator 210 may be used to produce x-ray sheet beam 220.

In one embodiment, the x-ray generator 210 has a large target 211 surface 209 area and can, therefore, operate at high peak and average power. If provided with adequate heat removal capacity, for example liquid cooling of the target 211 via a ferrofluidic seal, it can operate continuously with $\geq 100$ KW of input power. The rate at which a diffraction system can acquire data depends upon the detector efficiency. However, once the detector efficiency has been optimized the data acquisition rate scales directly with the available input x-ray power.

The limit on the throughput of the above diffraction system in a transportation center operating environment is likely to be set by available wall plug power. If this is, for example 50 KW, and the duty cycle for tube operation is less than 100% then an energy storage system (for example a compact flywheel unit) drawing a continuous 50 KVA can be use to increase the available power input to the tube during its on time. If the tube operates with a 50% duty cycle it could be operated with 100 KW of input power.

Referring again to FIGS. 2A and 2B, the x-ray sheet beam 220 is directed to a container 240 on a conveyor 250 as the conveyor moves the container 240 in direction 243 through the axis of the x-ray sheet beam 220. The x-ray sheet beam 220 passes vertically through the container 240 to be scanned as it moves along conveyer 250 in direction 243. Alternatively, the container 240 to be scanned need not be on a conveyor 250, but may be positioned under the x-ray sheet beam 220 through other means. In one embodiment, the width of the x-ray beam 220 is selected to cover, for example the whole width (e.g., 242) of container 240. Alternatively, the x-ray beam 220 may have a width 249 greater than the width of conveyor 250 (as illustrated in FIG. 2B). The x-ray sheet beam 220 may have widths, for example, in the approximate range of 2 mm to 2 meters as determined by the width of the x-ray target 211.

If the x-ray sheet beam 220 intercepts a crystalline material in the container 240 (e.g., a plastic explosive), x-ray photons are diffracted at an angle ($\theta$) 264 to the incident x-ray beam. The angle 264 depends upon the d-spacing of the atomic planes in the material. The trajectories of the diffracted photons lie on cones (e.g., cone 260) with half angle $\theta$ centered on the beam axis. The diffracted x-rays 265 are detected and their properties measured by a detector assembly 270 located below the conveyer 250 and displaced laterally from the path of the primary sheet beam so that the detector assembly 270 collects the diffracted x-rays 265. A linear detector 290 may be positioned underneath the conveyor at the primary axis of the x-ray sheet beam 220 to detected undiffracted components of the x-ray sheet beam 220. The linear detector (e.g., composed of a line of photoconducting diodes) measures the undiffracted x-ray beam and provides a reference signal and projection line scan image of container 240.

Figure 2C:
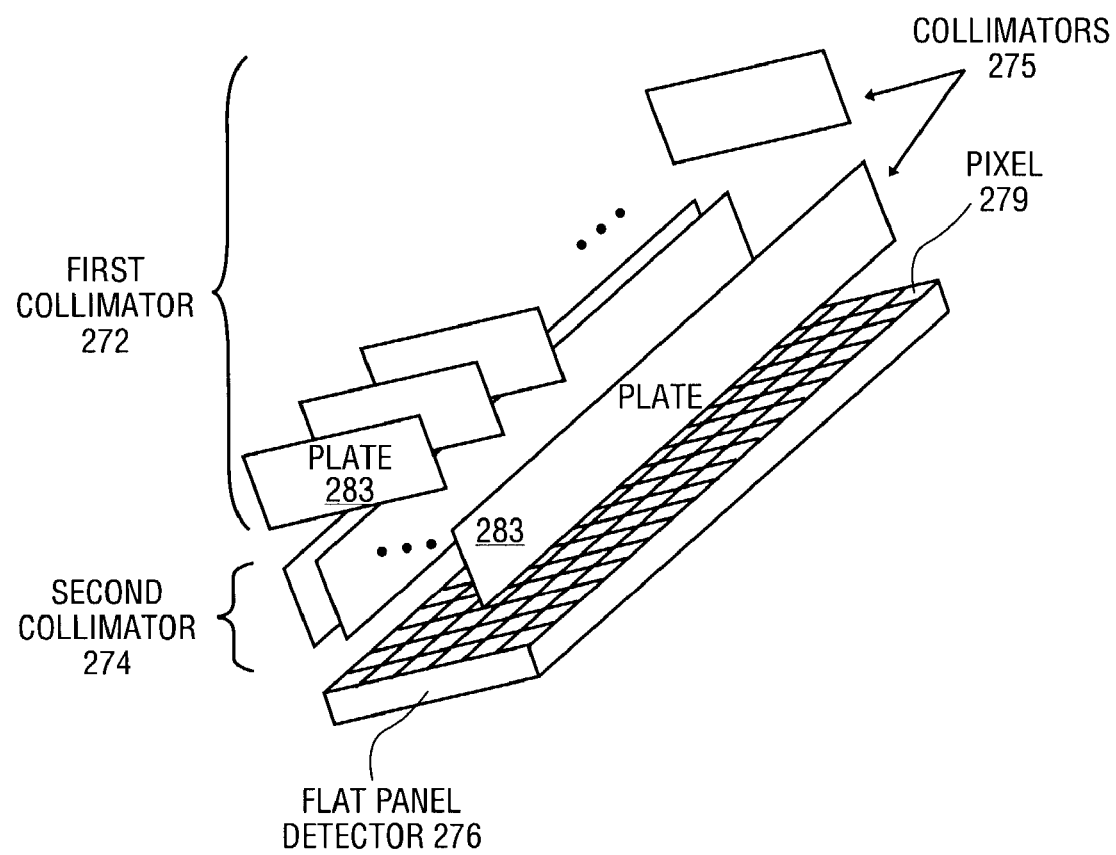
FIG. 2C illustrates one embodiment of a pair of collimators having orthogonal collimation planes with respect to each other.

In one embodiment, the detector assembly 270 may include first and second collimators 272 and 274 and a flat panel detector 276. The flat panel detector 276 may have a conventional TFT structure with a scintillator or photoconductor x-ray direct conversion layer, as discussed below in relation to FIGS. 5A and 5B. In one embodiment, the conversion layer is amorphous and, in particular, may have a polycrystalline structure. Alternatively, the conversion layer may have other crystalline structures. The detector assembly 270 may be configured to have a narrow acceptance angle of approximately 0.2 degrees full width at half maximum (FWHM) by using one or more collimators placed in front of the flat panel detector 276. The collimation planes of the first collimators 272 plates (e.g., plate 283) and the second collimator 274 plates (e.g., plate 293) may be substantially orthogonal to each other, as illustrated in FIG. 2C. The collimators 275 ensure that each pixel 279 of the flat panel detector 276 views a separate area of the beam, thus dividing the diffracted x-rays 265 into volume elements. In particular, first collimator 272 divides the x-ray sheet beam into individual vertical (e.g., beam direction 241 mapping to flat panel detector length 271) segments and second collimator 274 provides the angular resolution for accepting diffracted x-rays of a particular angle. Photons having a particular diffraction angle are selected by the angle of the collimators 275 and flat panel detector 276 with respect to the primary x-ray sheet beam 220. By tilting the second collimator 274 and flat panel detector 276 together, it is possible to scan through the diffraction spectrum in terms of diffraction angle. The first collimator 272 need not reside within the detector assembly 270, such that only the second collimator 274 and the flat panel detector 276 are movable. In an alternative embodiment, the plates of the first and second collimators may be integrated together to form a single collimator having orthogonal plates. Alternatively, other collimator arrangements known in the art may be used, for examples, hexagonal collimators.

In FIGS. 2A and 2B, only a single detector assembly 270 having a large area flat panel detector 276 is shown for clarity. Diffraction is symmetrical about the primary beam and multiple detector assemblies using smaller area flat panel detectors can be located on the radial periphery of cone 260 such as, for example, on diametrically opposed sides of the primary sheet beam (as discussed below in relation to FIG. 4B), for improved sensitivity and signal to noise. In one embodiment, a pair of Soller collimators may be used. Soller collimators are compact collimators obtainable with a FWHM acceptance angle of 0.16° with greater than 70% transmission and are commercially available from JJ X-Ray of Denmark.

By collecting the diffracted x-rays from each volume element (voxel), it is possible to detect, identify and physically locate substances (e.g., explosives) within container 240 as it is moved through the x-ray sheet beam 220. The method is substance-specific and sensitive, with sub-voxel detection capability because the substance does not need to fill an entire voxel to be identified. The requirement is merely that sufficient material of the substance is intersected by the x-ray sheet beam 220 to give a diffracted photon signal that is above the detector noise level.

The diffracted x-rays may be characterized in different ways, for examples, by wavelength dispersive (WD) diffraction and energy dispersive (ED) diffraction. In wavelength dispersive diffraction, an incident x-ray beam may be composed of monochromatized x-rays containing a narrow range of wavelengths typically 1% or less, centered upon an x-ray emission line characteristic of the x-ray target material, for example, a K-alpha line, to increase the photon flux in the monochromatized beam. The incident beam may be monochromatized, for examples, by diffraction off a crystal, by absorption edge filtering, via a graded multilayer mirror, or by other means known in the art. The latter has the advantage of improved x-ray collection efficiency.

In one embodiment, a copper (Cu) target generating filtered Cu K-alpha radiation is used for the x-ray source. The radiation's 1.54 Å wavelength results in large diffraction angles that can be measured with high precision. However, Cu K-alpha radiation is rapidly attenuated even by atmospheric air and more energetic x-ray photons may be necessary for container scanning where the radiation must penetrate the full thickness of a container which may contain strongly absorbing objects.

As such, in alternative embodiments, other types of targets 211 generating other types of radiation may be used for the x-ray source. In one embodiment, radiation having energy in the approximate range of 30 to 120 KeV is used. Even higher energies may be used for still greater penetrating power but at the cost of decreased diffraction angles. In one particular embodiment, for example, a tungsten (W) target 211 generating W K-alpha characteristic radiation, with a photon energy of 59.3 KeV and wavelength of 0.21 Å, may be more suitable for checked bag scanning. There is the added advantage that a tungsten target can be operated with high beam voltage and at high beam power. The x-ray output rises with both beam voltage and the atomic number of the target material. Thus a tungsten target is a more efficient producer of x-rays than a copper target. The tradeoff is reduced diffraction angles due to the shorter x-ray wavelength.

Figure 3:
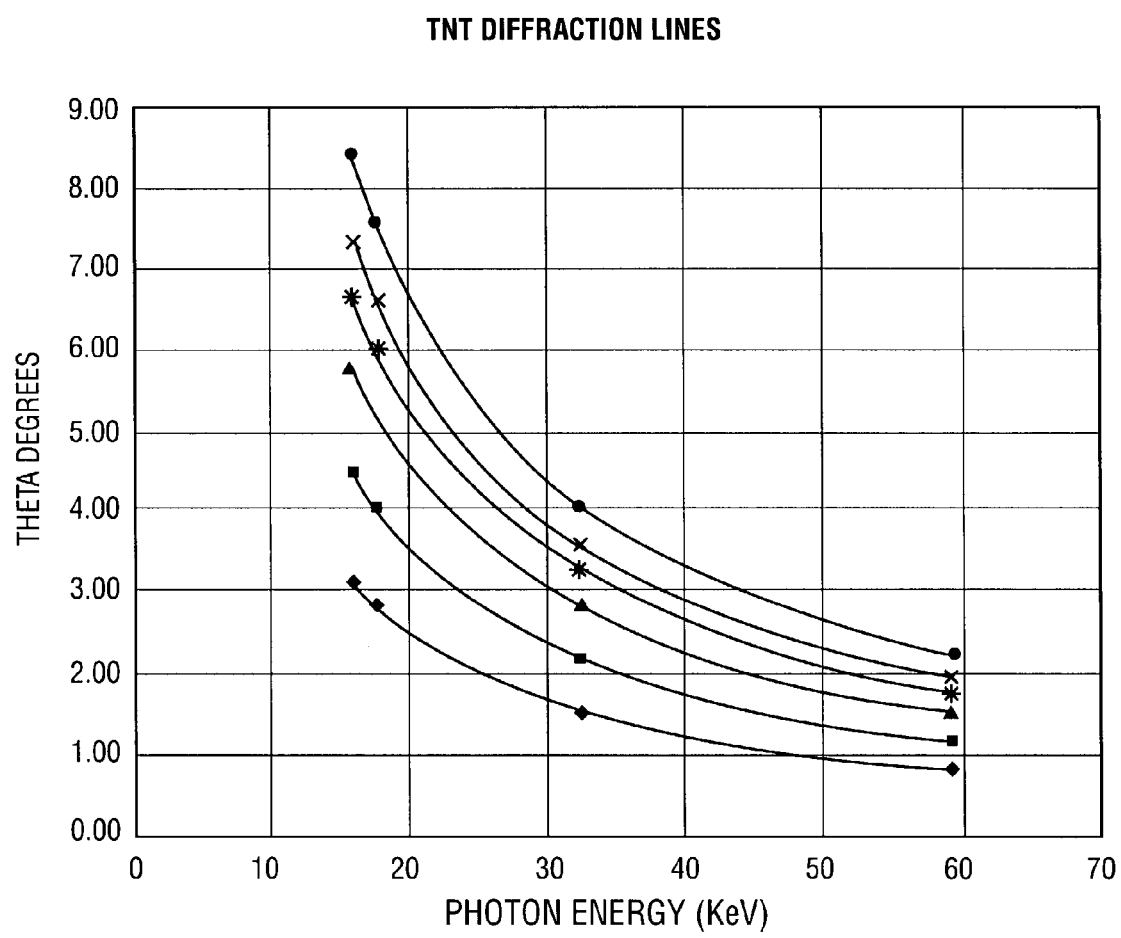
FIG. 3 shows a plot of diffraction angle against x-ray photon energy for the six strongest diffraction lines of trinitrotoluene (TNT).

FIG. 3 shows a plot of diffraction angle against x-ray photon energy for the six strongest diffraction lines of trinitrotoluene (TNT), which has d-spacings typical of organic explosive compounds that might be encountered in a terrorist device. The range of angles at the 59.3 keV energy of W k-alpha is of the order of 2.5°. With W K-alpha radiation in WD mode and measurement of crystal d-spacings down to 1.5 Å, the minimum value required for explosives screening, $\theta$ reaches a maximum of just over 4°. This parameter, together with the vertical height of the container 240 to be scanned, may be used, in one embodiment, to determine the required detector size in the direction 243 parallel to the conveyer motion.

In x-ray crystallography, highly accurate measurement of diffraction angles is necessary for structure determination. The requirements are less stringent for matching a diffraction spectrum to a database of spectra of threat compounds. The angular discrimination provided by a simple collimator system placed in front of the detector is sufficient to resolve "fingerprint" spectra adequate for matching purposes. For example, if the W k-alpha diffraction spectrum of TNT is convolved with the 0.16° FWHM of a commercial Soller collimator, the diffraction lines show significant broadening but the line definition is still adequate for identifying proscribed material by comparison with reference spectra.

Figure 4A:
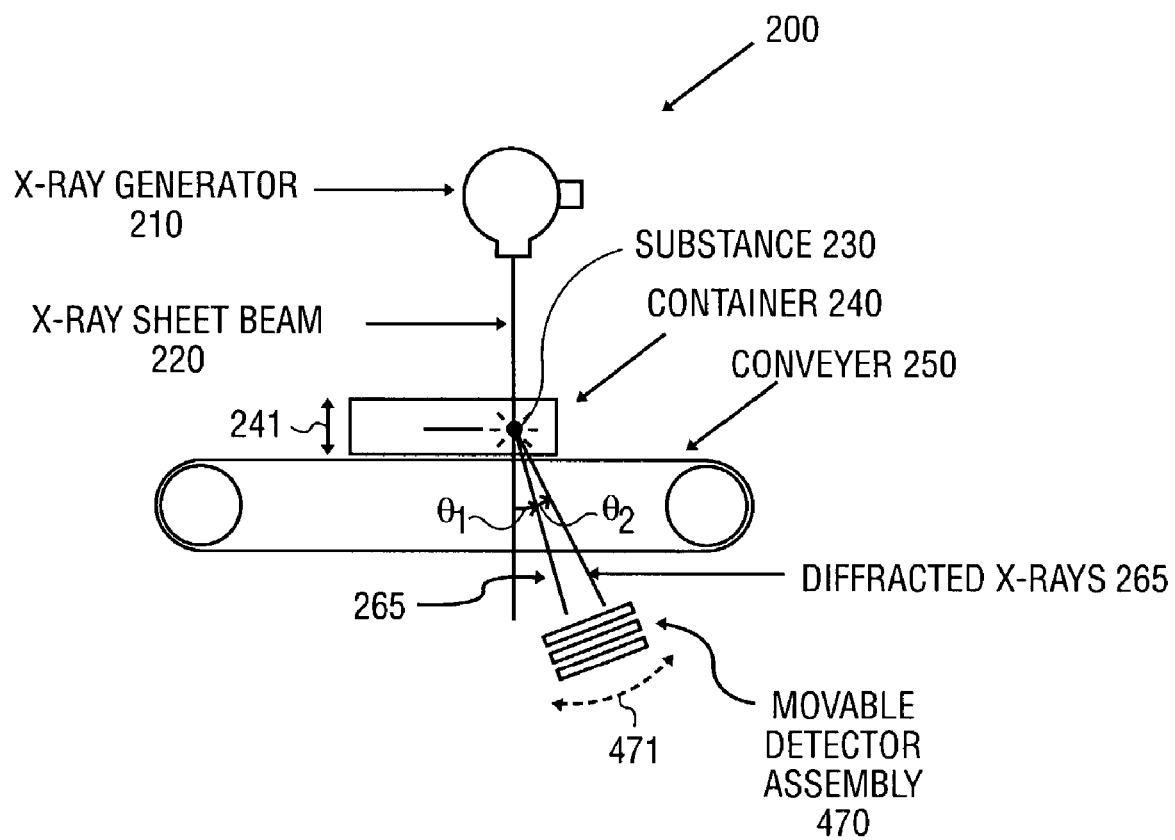
FIG. 4A illustrates one embodiment of an x-ray diffraction system having a movable detector assembly.

FIG. 4A illustrates one embodiment of x-ray diffraction system 200 having a movable detector assembly 470 that may be used for operation with wavelength dispersive diffraction. As previously discussed, in the WD mode the x-ray source of generator 210 is filtered so that the x-ray sheet beam 220 contains only a narrow range of x-ray photon wavelengths that are centered upon, for example, the W K-alpha line. In WD mode, the x-ray diffraction lines 265 (only two exemplary diffraction lines are illustrated) are scanned by moving (e.g., by tilting, pivoting, rotating, sliding, etc.) 471 the detector assembly 470 from an angle $\theta_1$ to an angle $\theta_2$ on the order of a few degrees. For example, for W K-alpha radiation, the angular extent of the scan may be of the order of 2.5 degrees to cover the range of d-spacings that is of interest for the detection and identification of explosives. With W K-alpha radiation in the WD mode and measurement of crystal d-spacings down to 1.5 Å, the maximum value of $\theta$ may be approximately 4 degrees. Alternatively, another angular range $\theta_2-\theta_1$ may be used based on the particular substance to be detected. The conveyor 250 stops the container 240 at each scan location and container 240 is scanned serially through the angles $\theta_1$ to $\theta_2$ that the x-ray sheet beam 220 is diffracted through. The vertical position in the incident x-ray sheet beam direction 241 maps onto the flat panel detector 276. This mapping changes with the angle $\theta$ at which the detector assembly 470 is positioned with respect to the primary axis of the x-ray sheet beam 220. A software routine may be used to perform such a mapping.

Referring again to FIG. 2B, the vertical dimension 441 of the scanned area is compressed by a factor of sine $\theta$ in the diffracted image on the surface of flat panel detector 270 (and 470 of FIG. 4A). Thus, for example, a 100 cm wide 242×75 cm high 241 scanned area in container 240 maps onto a 100 cm wide 272×5.25 cm long 271 flat panel detector area. In practice, the flat panel detector 276 need not be in the form of a single elongated panel (e.g., 100 cm×5.25 cm). Since x-rays are diffracted symmetrically outwards, the flat panel detector 276 can be divided into several smaller panels, as illustrated in FIG. 4B.

Figure 4B:
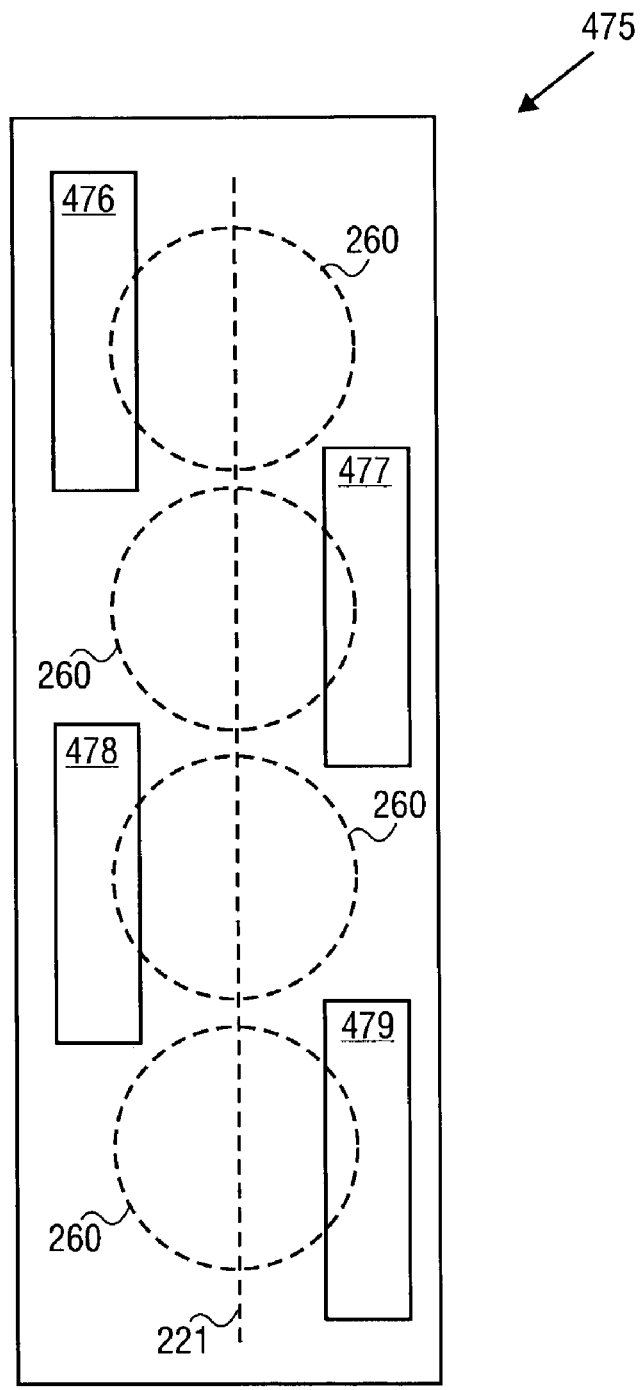
FIG. 4B is a top view along the primary axis of the x-ray sheet beam of a diffraction system illustrating one embodiment of a detector assembly.

FIG. 4B is a top view along the primary axis of the x-ray sheet beam of system 200 illustrating one embodiment of a detector assembly. Continuing the above example, the flat panel detector 475 may be divided into four panels 476-479, each panel with active area of 25 cm×5.25 cm, located alternately on either side of the x-ray sheet beam primary axis 221. In yet another embodiment, the panels residing on a side of primary axis 221 may be disposed within a separate assembly (e.g., panels 476, 478 in one assembly and panels 477 and 479 in another assembly) or each panel may be disposed within its own assembly.

Figure 5A:
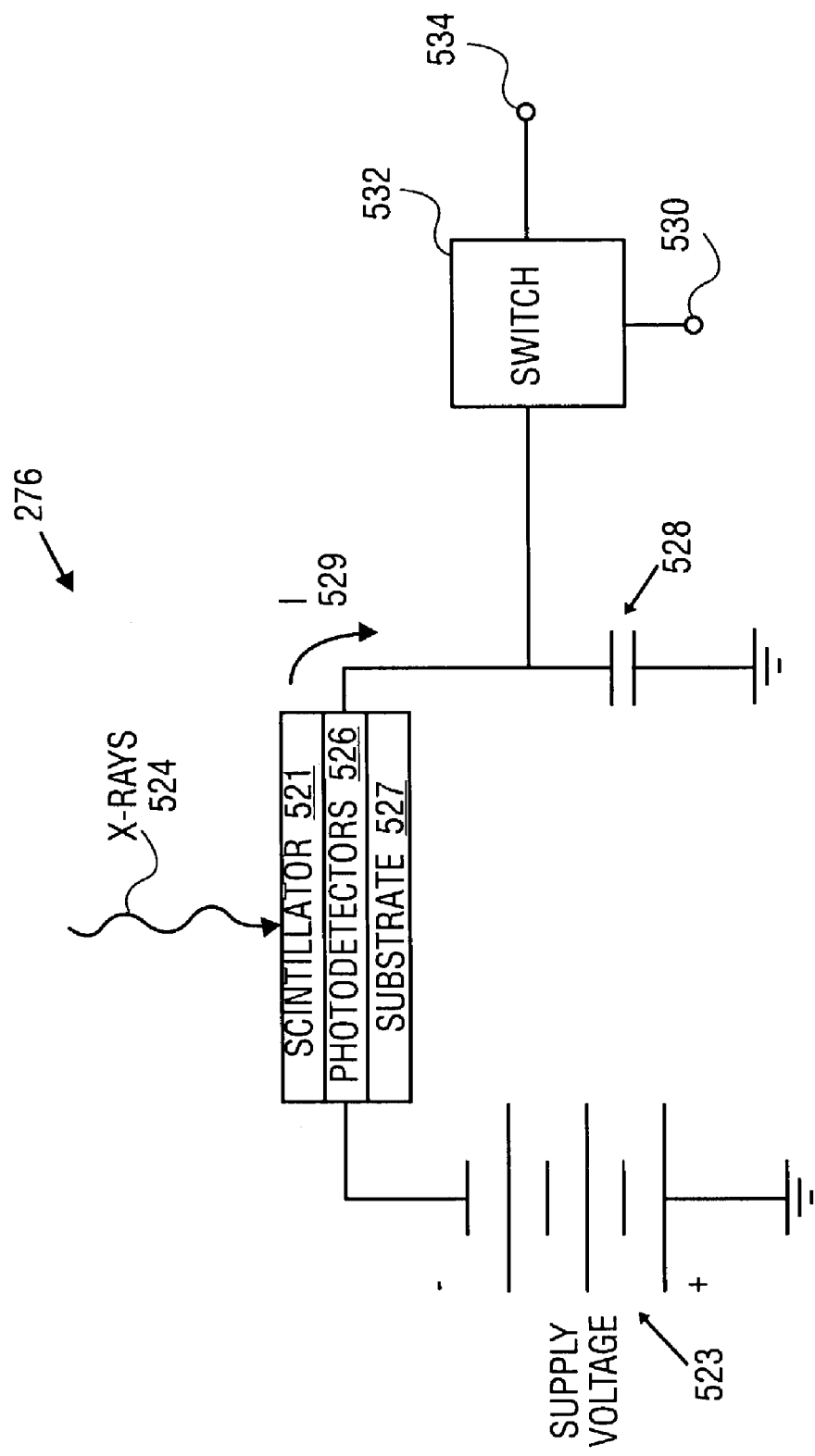
FIG. 5A illustrates one embodiment of components of a flat panel detector.

FIG. 5A illustrates one embodiment of components of a flat panel detector. The flat panel detector 276 may be constructed as a panel with a matrix of photosensitive devices with readout electronics to transfer the light intensity of a pixel to a digital video signal for further processing or viewing. Flat panel detector 276 includes a conversion layer formed by a scintillator layer 521 and a photodetector layer 526. Flat panel detector 276 also includes a substrate 527, a supply voltage 523, capacitor 528, and switch 532. In one embodiment, for example, photodetector layer 526 may include photoconductors or photovoltaic components (e.g., a photodiodes) that receive light photons from a scintillator 521. The scintillator 521 is a conversion layer that receives x-rays and generates visible light that strikes photodetector layer 526. Photodetector layer 526 captures the visible light produced in the scintillator and generates an electric current (I) 529. The electric current 529 charges capacitor 528 and leaves a charge value on capacitor 528, where the integrated charge on capacitor 258 is proportional to the integrated light intensity striking photodetectors 526 for a given integration time. Capacitor 528 is coupled to switch 532 such as a thin-film-transistor (TFT). The operation of switch 532 may be discussed herein in relation to a TFT for ease of discussion purposes only. Other types of switch devices, for example, switching diodes may also be used.

At an appropriate time, the control input 530 (e.g., gate of a TFT) activates switch 532 and reads out the charge on capacitor 528 at node 534. The charge at node 534 is further amplified and processed for a corresponding pixel of flat panel detector 276, as discussed below in relation to FIG. 7.

Figure 5B:
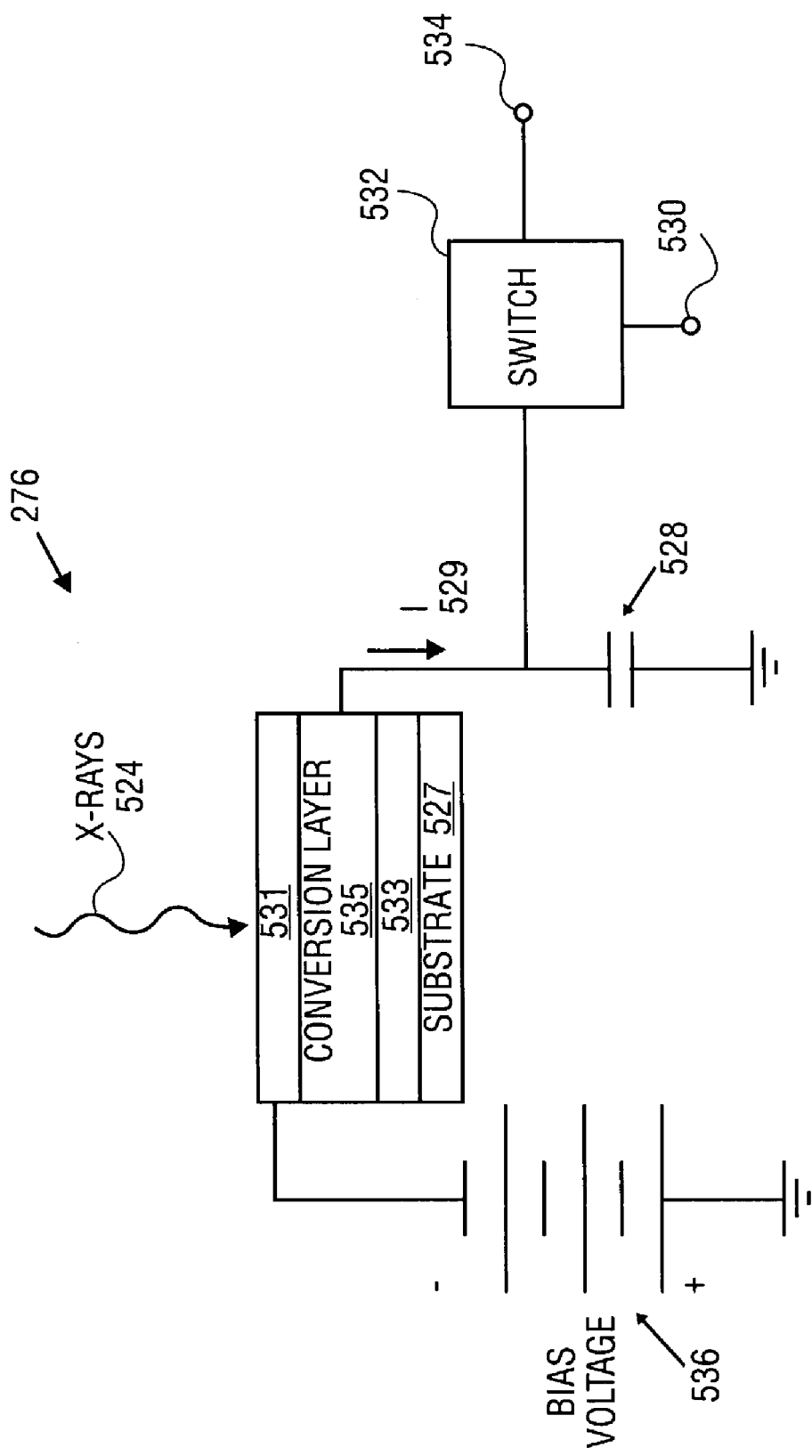
FIG. 5B illustrates one embodiment of a flat panel detector having a direct conversion layer.

In an alternative embodiment, flat panel detector 276 may have other configurations. For example, flat panel detector 276 may utilize a semiconductor material as a direct conversion layer to convert x-rays to electric charges directly, without an intermediate step of converting x-rays to visible light. FIG. 5B illustrates one embodiment of flat panel detector 276 having a direct conversion layer 535. The flat panel detector 276 has conversion layer 535 composed of a semiconductor material disposed between a top electrode layer 531 and charge-collection electrode layer 533. A bias voltage 536 is applied across semiconductor layer 535 incident to the top electrode 531. As x-rays 524 propagate through the semiconductor layer 535 through the top electrode 531, it creates electric charges within the semiconductor layer 535 that are drawn to the charge-collection layer 533. The charge is collected, amplified and processed for a corresponding pixel of flat panel detector 276.

A significant increase in detector sensitivity can be gained by utilizing a flat panel detector 276 coated with a wide bandgap (e.g., in the approximate range of 0.5 to 3 eV) semiconductor as a conversion layer 535. Semiconductors act as direct conversion materials. The passage of x-ray photons generates electrons and holes that are swept out of the photoconducting conversion layer 535 by an applied bias voltage and collected on a switch (e.g., TFT) array. In one embodiment, a polycrystalline mercury-iodide ($HgI_2$) may be deposited on TFT panels to form direct detection arrays with very high sensitivity, approaching the theoretical maximum. This sensitivity may be more than five times better than that of flat panel detectors with scintillator layers that employ indirect conversion.

It should be noted that alternative configurations and components known in the art may be used with flat panel detector 276. For example, the flat panel detector 276 may be integrated with CCD-based or CMOS-based photodetectors. Flat panel detectors are available from manufacturers such as Varian Medical Systems, Inc. of California.

Figure 6:
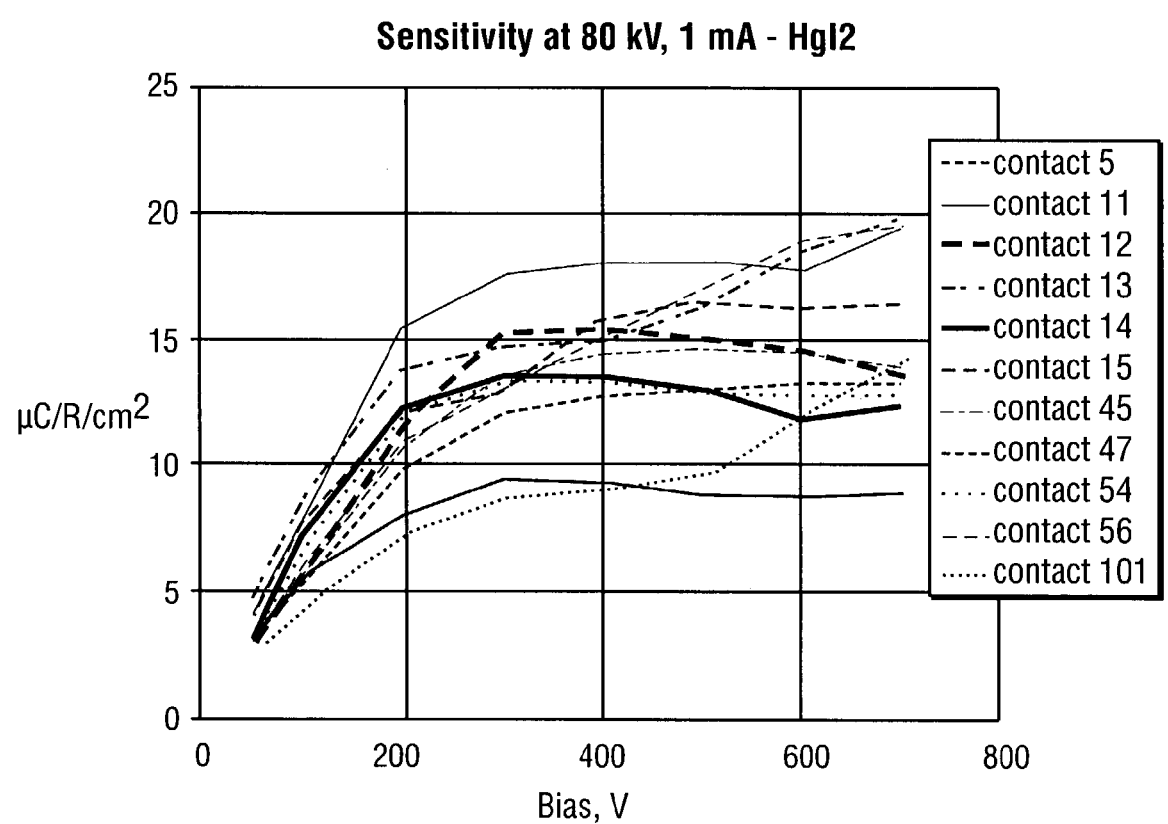
FIG. 6 is an exemplary figure showing the x-ray sensitivity of a polycrytalline $HgI_2$ detector layer operating at room temperature with 80 KV(p) photons.

FIG. 6 shows the x-ray sensitivity of an exemplary polycrystalline $HgI_2$ detector layer operating at room temperature with 80 KV(p) photons. The material has sensitivity in the range of 15 µCoulombs/R/cm$^2$ that is approximately five times higher than some of the better performing CsI scintillator materials. The curves of sensitivity versus bias voltage show saturation at a bias field below 1volt/micron that is important to avoid voltage dependent gain variations during operation at high signal levels.

Although detector 276 may be operated at room temperature, detector 276 may also be cooled below room temperature (e.g., down to approximately minus 100 degrees C.) in order to reduce dark current contributions to the collected charge on the capacitors 528 of the detector 276. Cooling of a semiconductor conversion layer detector results in lower noise and permits a higher bias voltage. The latter improves the rate at which charge carriers are swept out of the semiconductor, which increases the maximum attainable count rate for photons and improves the energy resolution. Wide band-gap semiconductors have relatively low dark currents even at room temperature and the dark current has a steep dependence upon temperature. Although operation at liquid nitrogen temperature is not required, cooling semiconductors such as $HgI_2$ to temperatures of the order of minus 30° C. is beneficial, with a somewhat lower optimum operating temperature for CZT. These temperatures can be reached, for examples, with a solid state Peltier cooler (down to approximately minus 70° C.). Peltier coolers, also known as thermoelectric coolers, are solid state heat pumps that take advantage of the Peltier Effect. The Peltier effect takes place when an electric current is sent through two dissimilar materials that have been connected to one another at two junctions. One junction between the two materials is made to become warm while the other becomes cool, in what amounts to an electrically driven transfer of heat from one side of the device to the other. Peltier coolers are available from different manufacturers such as Swiftech of California, USA. In alternative embodiments, other temperatures and other types of cooling systems may be used, for example, a closed circuit cascade cooling system (e.g., available from IGC Polycold Systems of California, USA) that can cool as low as approximately minus 100° C.

Figure 7:
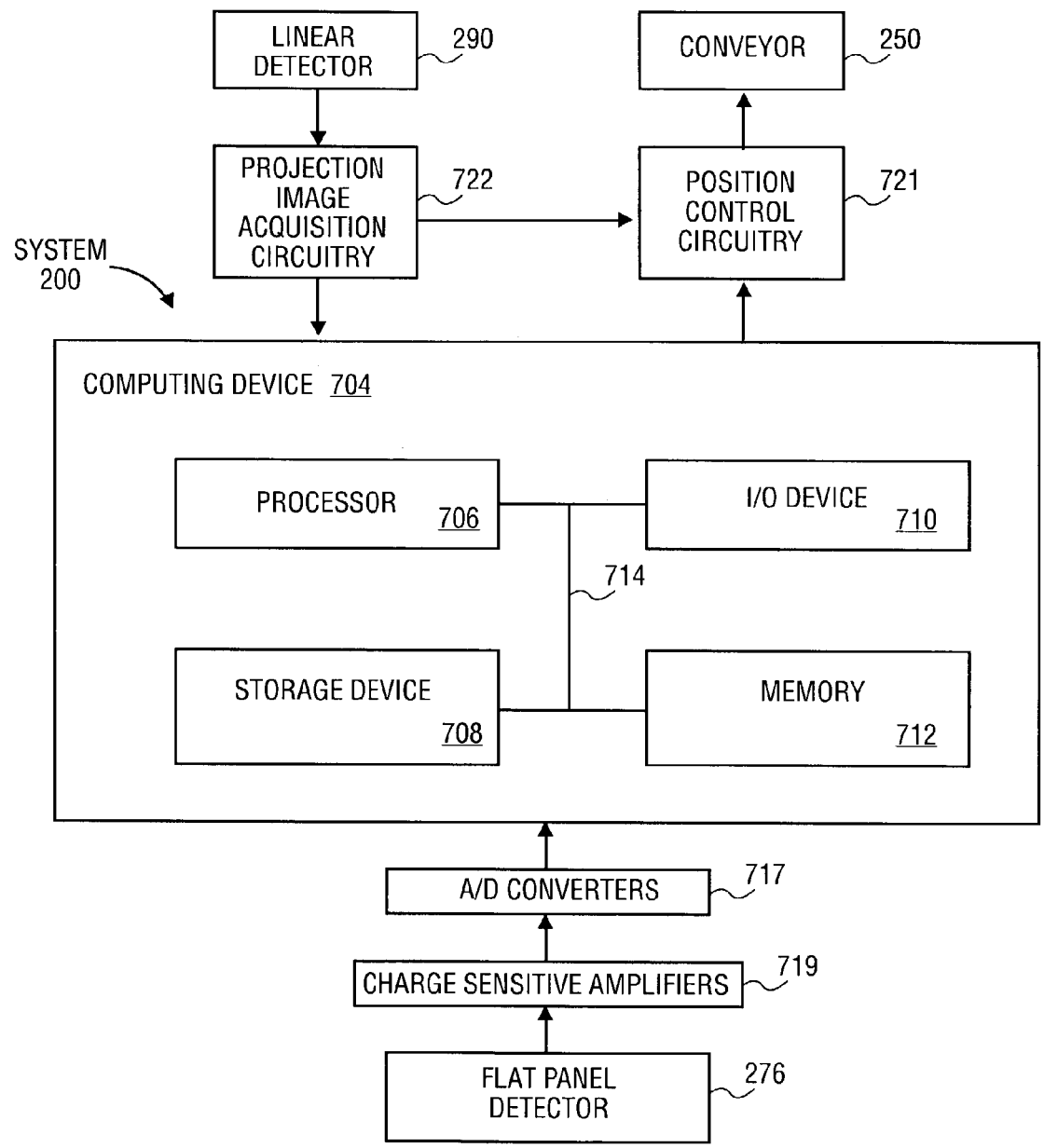
FIG. 7 illustrates one embodiment of electronic components of the scanning

FIG. 7 illustrates one embodiment of, in particular, electronic components of the scanning system 200. Scanning system 200 includes a computing device 704 coupled to a flat panel detector 276. As previously discussed in relation to FIGS. 5A and 5B, flat panel detector 276 operates by accumulating charge on capacitors (e.g., capacitor 528) generated by pixels (e.g., pixel 279 of FIG. 2C) of photodetectors with a scintillator layer 521 or by pixels of a direct conversion layer 535. Typically, many pixels are arranged over a surface of flat panel detector 276 where, for example, TFTs (or e.g., single and/or double diodes) at each pixel connect a charged capacitor 528 to charge sensitive amplifier 719 at the appropriate time. Charge sensitive amplifier 719 drives analog to digital (A/D) converter 717 that, in turn, converts the analog signals received from amplifier 719 into digital signals for processing by computer device 704. A/D converter 717 may be coupled to computing device 704 using, for example, I/O device 710 or interconnect 714. A/D converter 717 and charge sensitive amplifiers 719 may reside within computing device 704 or flat panel detector 276 or external to either device. Amplifiers 719 count the photons received by flat panel detector 276 and provide a pulse proportional to the received energy. Amplifiers 719 transmit the pulse to A/D converter 717. A/D converter 717 converts the pulse heights to a digital value that is provided to computing device 704.

The methods, steps, instructions, etc. that are performed by computer device 704, as discussed below, may be performed by hardware components or may be embodied in machine-executable instructions (or a combination thereof), which may be used to cause a general-purpose or special-purpose processor programmed with the instructions to perform the steps. Machine-executable instructions may be contained in machine readable medium that includes any mechanism for storing or transmitting information in a form (e.g., software, processing application) readable by a machine (e.g., a computer). The machine-readable medium may includes, but is not limited to, magnetic storage medium (e.g., floppy diskette); optical storage medium (e.g., CD-ROM); magneto-optical storage medium; read only memory (ROM); random access memory (RAM); erasable programmable memory (e.g., EPROM and EEPROM); flash memory; electrical, optical, acoustical or other form of propagated signal (e.g., carrier waves, infrared signals, digital signals, etc.); or other type of medium suitable for storing electronic instructions. Particular reference to hardware or software herein is made only for ease of discussion.

Computing device 704 is coupled to conveyor 250 to control the position of container 240 through, for example, position control circuitry 721. Computing device 704 is coupled to projection image acquisition circuitry to 722 to receive signals indicative of the undiffracted x-ray beam from linear detector 290 and provide a projection line scan image of container 240. Computing device 704 implements the methods for processing of the digital signals provided by A/D converter 717 to provide an output for identification of the substance being scanned as is known in the art. In one embodiment, computing device 704 includes a processor 706, storage device 708, input/output (IO) device(s) 710, and memory 712 that are all coupled together with interconnect 714, such as a bus or other data path.

Processor 706 represents a central processing unit of any type of architecture (e.g., Intel architecture or Sun Microsystems architecture), or hybrid architecture. In addition, processor 706 could be implemented in one or more semiconductor chips. Storage device 708 represents one or more mechanisms for storing data and/or instructions such as the method steps of the invention. Storage device 708 represents read-only memory (ROM), random access memory (RAM), magnetic disk storage media, optical storage media, flash memory devices, and/or other machine-readable media. Interconnect 714 represents one or more buses (e.g., accelerated graphics port bus, peripheral component interconnect bus, industry standard architecture bus, X-Bus, video electronics standards association related buses, etc.) and bridges (also termed bus controllers). I/O device(s) 710 represents any of a set of conventional computer input and/or output devices including, for example, a keyboard, mouse, trackball or other pointing device, serial or parallel input device, display monitor, plasma screen, or similar conventional computer I/O devices. Memory 712 represents a memory device for retaining data and processor instructions for processor 6 according to the method steps of the invention. Memory 712 can be implemented using any of the memory devices described above for storage device 8. In addition, memory 712 can be used as a data cache for processor 706. It should be noted that the architecture illustrated in FIG. 7 is only exemplary. In alternative embodiments, other architectures may be used for computing device 704. For examples, computing device 704 may utilize memory controller(s) and/or I/O controller(s) that are dedicated or integrated into one or more components. For other examples, while computing device 704 is described in relation to a single processor computing system, a multi-processor computing device may be used and/or a distributed computing environment may be used where the machine readable medium is stored on and/or executed by more than one computing devices.

Referring again to FIGS. 2A and 2B, an alternative method of obtaining diffraction data from the contents of the container is to position the collimator and detector assembly at a fixed angle to the incident beam. If the acceptance angle θ for photons is fixed then, from the Bragg equation, specific x-ray photon wavelengths will be diffracted from the various crystal lattice d-spacings at a given diffraction angle. The photon wavelengths, and hence energies, are defined by the lattice spacings and the selected photon acceptance angle. Energy dispersive diffraction scanning may be capable of much more efficient use of the x-rays from the line-source x-ray tube, coupled with the ability to scan through the entire diffraction spectrum in parallel rather than serially.

For energy dispersive diffraction the x-ray sheet beam does not need to be monochromatic but may be merely collimated directionally by techniques known in the art. As such, much greater total power in the continuum output of source can be used. With energy dispersive diffraction scanning, the incident x-ray sheet beam 220 contains a broad range of photon energies. Each wavelength has an associated photon energy. The smaller the wavelength, the higher the photon energy. The unfiltered bremsstrahlung radiation from, for example, a tungsten (W) target contains a suitable spread of photon energies. Alternatively, other materials for target 211 may be used. The incident electron beam energy is chosen to furnish a sufficiently high cut-off in the x-ray photon energy.

The appropriate photon takeoff angle may be derived by simulation or empirical data. For example, FIG. 3 that shows the diffraction lines of TNT. As the diffraction angle θ is increased, the diffracted photon energies shift downwards. Lower photon energies will be preferentially absorbed during passage through the container. A photon takeoff angle of 2–2.5° results in an appropriate range of photon energies for detection of TNT.

The flat panel detector 276 is provided with a photoconductor layer 535 capable of providing a pulse height output that is proportional to the energy of the photons incident on the detector. Photoconductors that may be used for conversion layer 535 include, for examples, CZT, $HgI_2$, $PbI_2$, Se or other wide bandgap semiconductor materials. The acceptance angle of the panel for incident photons may be defined by the collimator(s) in a similar manner to the wavelength dispersive arrangement. However, the acceptance angle may be held constant (e.g., typically 2–3 degrees away from the sheet beam axis). In this case, specific x-ray photon energies are diffracted by the d-spacings of the material at this chosen angle. Only photons with these specific energies can pass through the collimator 274 at the selected angle. The flat panel detector 276 measures the energy of the diffracted photons, thus characterizing the material. This method has the advantage that the energy data can be measured in parallel, hence greatly increasing the scan speed. Additionally, a mono-energetic primary x-ray sheet beam 220 is not required and the entire continuum output of the x-ray generator 210 can be used that increases the efficiency of x-ray generation and utilization in the incident x-ray sheet beam 220.

Figure 9:
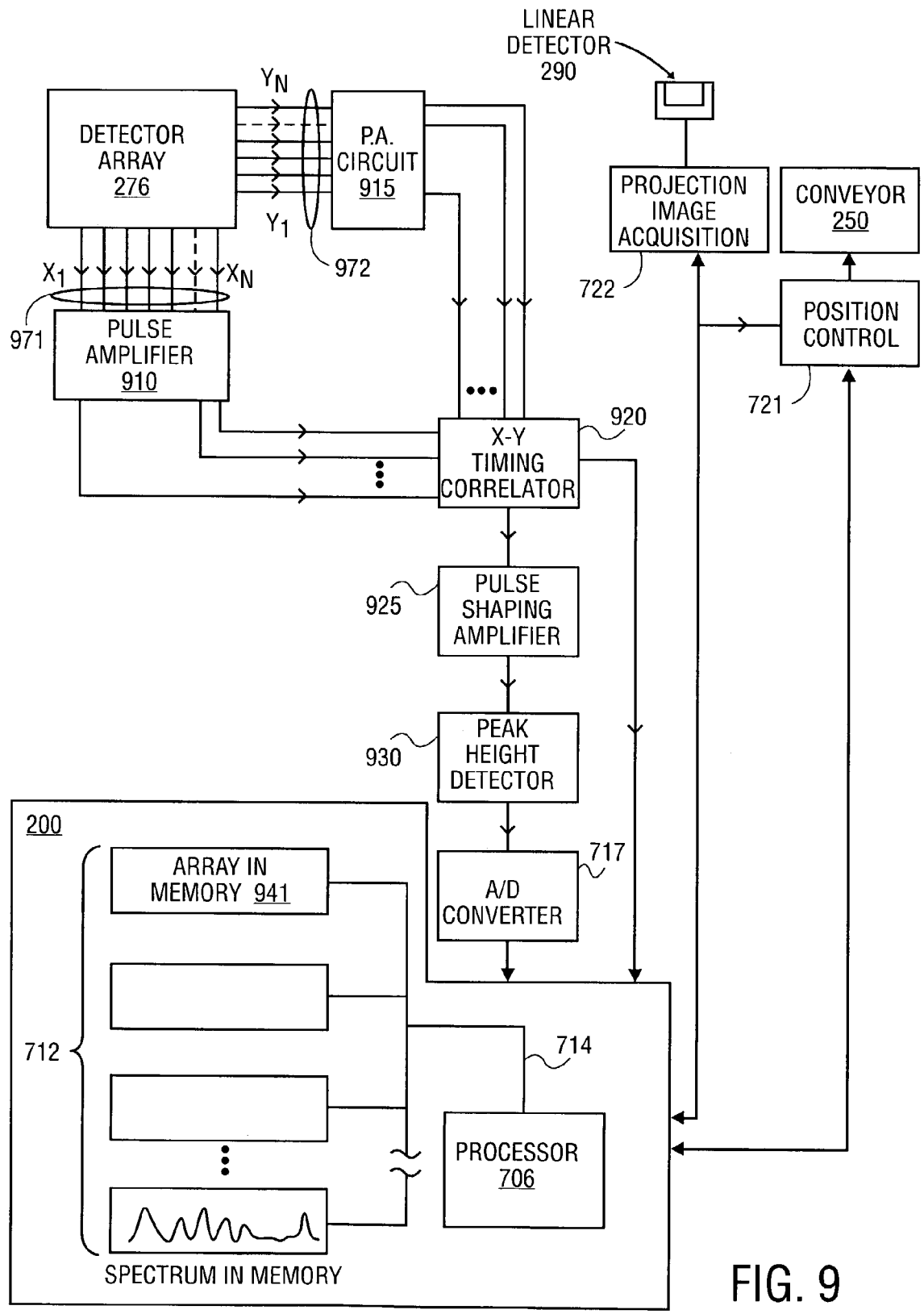
FIG. 9 illustrates an alternative embodiment of a flat panel detector that may be used with an energy dispersive mode of scan operation.

In an alternative embodiment, the electronic components of flat panel detector 276 and scanning system 200 may be modified from that shown in FIGS. 5A, 5B, and 7 for use with the energy dispersive mode. FIG. 9 illustrates an alternative embodiment of a flat panel detector that may be used with an energy dispersive mode of scan operation. In this embodiment, with reference to FIGS. 5B, 7 and 9, flat panel detector 276 includes an array of pixels having two sets of parallel conductor lines on the top and bottom of a semiconductor conversion layer (e.g., conversion layer 535 of FIG. 5B). A set of conducting read-out lines ($X_1$ to $X_N$) 971 runs in the x-direction on the top face and a set of conductors ($Y_1$ to $Y_N$) 972 runs in the y-direction on the bottom face of the semiconductor layer 535. A bias voltage 536 is applied through the thickness of the semiconductor layer 535 between the set of x lines 971 and the set of y lines 972. Pulse measurement circuits may be disposed around the periphery of the detector array 276 to measure pulses, as the pulses appear on the x and y lines 971 and 972, respectively.

The pulse measurement circuits may include pulse amplifiers (PA) 910 and 915, timing correlator 920, pulse shaping amplifier 925, and peak detector 930. The output of amplifiers 910 and 915 may be coupled to timing correlator 920. Timing correlator 920 uses coincidence timing to assign an x-y line pair to a particular pulse event, thereby localizing the position (pixel) at which the charge originated in the semiconductor layer 535. The pulses of charge are passed though a pulse shaping amplifier 925. In one embodiment, for example, the pulse shaping amplifier 925 may have a time resolution of the order of 2–20 microseconds that gives an output pulse proportional to the charge delivered in the initial pulse. The output pulse is fed to a peak detector 930 and an A/D converter 917 where the pulse amplitudes are converted to a digital value. The resulting A/D output is used as the address of a memory location in an array (e.g., array 941) of a digital memory 712. In effect, the memory arrays act as a series of individual counters each covering a narrow range in energy. Counts are accumulated in these "bins" or "channels" building up a digital representation of the energy distribution of the diffracted photons, which is the diffraction spectrum in the energy domain. Each pixel in the detector array 976 has an associated array of digital memory addresses and a spectrum in the energy domain energy is accumulated for each 2-D pixel position in the detector. The pixels map back to the equivalent positions in the plane of the x-ray sheet beam 220 as it passes transversely through container 240.

Various alternatives may also be used. It is desirable to keep the pulse of charge from each incident photon separate from the pulse from subsequent photons. At high count rates, a second pulse may reach the amplifier before the pulse from the first photon is fully processed. This results in a phenomenon known as pulse pile-up of a total pulse that is a combination of two pulses. In one embodiment, pulse pile-up rejection circuits may be incorporated into the electronics.

Figure 5C:
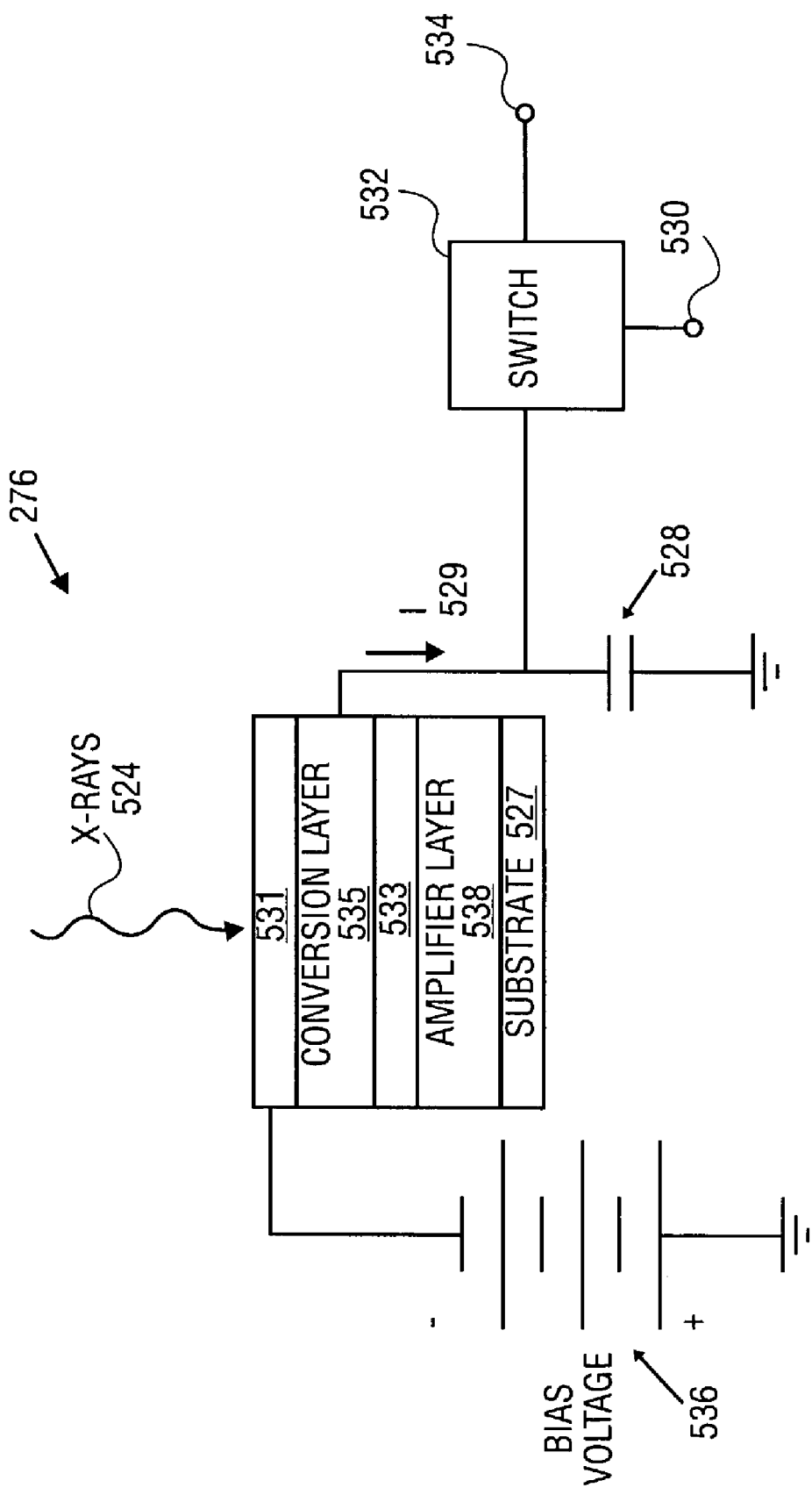
FIG. 5C illustrates an alternative embodiment of a flat panel detector having a direct conversion layer.

Considerable improvement in signal-to-noise can be achieved by locating a front-end amplifier at each pixel rather than having simple x-y read-out lines and peripheral read-out pulse measurement circuits. In one embodiment, for example, the front-end amplifier may be implemented as a layer 538 between the substrate 527 and the conversion layer 535 as illustrated in FIG. 5C.

In yet another embodiment, the x and y read-out lines 971 and 972 may also be incorporated into substrate 527. The top surface of semiconductor conversion layer 535 has a top electrode 531 in the form of a continuous conducting layer to which the bias voltage 536 is applied. Such a configuration may simplify fabrication of the flat panel detector 276 when using certain semiconductor materials for conversion layer 535 such as HgI$_2$ that are difficult to lay down contacts upon. A continuous contact sheet of, for example, evaporated palladium, may be easier to arrange than many narrow contact lines. Alternatively, other metal and metal alloys may be used for the contact layer 531. The x and y read-out lines 971 and 972 may be fabricated into substrate 527 at the same time as the pixel amplifier layer 538 before deposition of conversion layer 538. Each pixel would have a contact pad (defining the area of the pixel) above the amplifier in layer 533. The contact pads collect the pulse of the charge from semiconductor conversion layer 535, feed the pulse to the amplifier 538 that amplifies the pulse and provides it into the x-y lines in substrate 527.

In an embodiment where CZT is used as the conversion layer 535, the conversion layer 535 may have the form of a mosaic of tiles or strips of CZT supported upon a substrate. High performance CZT is not a polycrystalline material that can be deposited by physical vapor deposition (PVD) but is composed of monolithic single crystal pieces sliced from boules grown by high pressure Bridgeman crystallization. The same x-y read-out line scheme may be used and if individual pixel amplifiers are used they can be implemented, for example, as an amplifier layer 538 above the substrate 527 as illustrated in FIG. 5C. The amplifier layer 538 may be coupled to the CZT conversion layer 535, for example, by bump-bonding amplifier layer 538 to the underside of the CZT layer. Alternatively, other coupling methods may be used.

In one embodiment, the use of very large pixels (by display standards) in the diffraction detector makes it possible to subdivide each pixel into subpixels to reduce the performance requirement of the front end amplifier and read-out electronics. Each sub-pixel receives only a fraction of the photon flux incident on the pixel that reduces pulse pile-up and increases the maximum photon count rate under large signal conditions.

As previously discussed, a scintillator based detector may be used in pulse counting mode but is not commonly employed because of its low x-ray conversion efficiency compared to semiconductor direct conversion detectors. For the same x-ray photon energy deposited in the detector a factor of five or more electrons are obtained from a semiconductor detector as compared to a scintillator detector. This means that scintillator detectors have a lower signal to noise ratio and the lower absolute signal means less precision of energy measurement.

The 2D area flat panel detector discussed herein permits the spatial location of the of diffracted x-rays within container 240 where the searched-for substance is concealed. The cross section of the container 240 defined by the x-ray sheet beam 220 is mapped onto the flat panel detector 276 array surface with compression of the vertical direction 241. The use of a low cost, large-area, wide bandgap semiconductor detectors capable of single photon counting with adequate energy resolution would eliminate the constraints of existing scanning systems and permit single pass diffraction scanning at much higher speed. It should be noted again that the diffraction-based detection system discussed herein can detect almost any crystalline and, in particular, microcrystalline substance, including many illegal drugs and other contraband materials in addition to explosive materials.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense

What is claimed is:

1. An x-ray scanning system, comprising:
a conveyor;
an x-ray source configured to generate x-rays toward the conveyor; and
a flat panel detector to receive diffracted x-rays from a container moving on the conveyor through the x-rays;
a first collimator coupled to the flat panel detector; and
a second collimator disposed between the conveyor and the first collimator, wherein the first and second collimators have collimation planes orthogonal to each other.

2. The x-ray scanning system of claim 1, wherein the first collimator has collimation planes to divide the diffracted x-rays into individual vertical segments.

3. The x-ray scanning system of claim 1, wherein the scanning system has a detector assembly comprising the first collimator and the flat panel detector.

4. The x-ray scanning system of claim 3, further comprising a plurality of detector assemblies, each of the plurality of detector assemblies having the first collimator and the flat panel detector.

5. The x-ray scanning system of claim 4, wherein the x-rays generated toward the conveyor lay substantially in a plane and wherein at least one of the plurality of detector assemblies is disposed on an opposite side of the plane in relation to another of the plurality of detector assemblies.

6. The x-ray scanning system of claim 1, wherein the x-rays source generates an x-ray sheet beam having a width approximately in the range of 2 millimeters to 2 meters.

7. The x-ray scanning system of claim 1, wherein the x-ray source generates a plurality of parallel collimated beams.

8. The x-ray scanning system of claim 1, wherein the x-ray source comprises a target that generates radiation in the range of 30 to 120 KeV.

9. The x-ray scanning system of claim 8, wherein the target comprises tungsten.

10. The x-ray scanning system of claim 1, wherein the x-rays source generates an x-ray sheet beam.

11. The x-ray scanning system of claim 1, wherein the x-ray source generates a plurality of parallel collimated beams.

12. The x-ray scanning system of claim 1, wherein the x-ray source comprises a target that generates radiation in the range of 30 to 120 KeV.

13. The x-ray scanning system of claim 12, wherein the target comprises tungsten.

14. The x-ray scanning system of claim 1, wherein the flat panel detector comprises a conversion layer, wherein the conversion layer comprises an amorphous material.

15. The x-ray scanning system of claim 14, wherein the amorphous material is polycrystalline.

16. The x-ray scanning system of claim 14, wherein the conversion layer comprises a deposited semiconductor material having a bandgap in the approximate range of 0.5 to 3 eV.

17. The x-ray scanning system of claim 16, wherein the conversion layer comprises $HgI_2$.

18. The x-ray scanning system of claim 16, wherein the conversion layer comprises $PbI_2$.

19. The x-ray scanning system of claim 18, further comprising a cooling system coupled to the flat panel detector, and wherein the cooling system is operable to cool the flat panel detector down to approximately minus 30 degrees C.

20. The x-ray scanning system of claim 16, wherein the conversion layer has a surface area greater than 25 square centimeters.

21. The x-ray scanning system of claim 16, wherein the conversion layer has a surface area in the approximate range of 25 to 2,250 square centimeters.

22. The x-ray scanning system of claim 1, wherein the flat panel detector has a surface area greater than 25 square centimeters.

23. The x-ray scanning system of claim 1, wherein the flat panel detector is configured to operate at room temperature.

24. The x-ray scanning system of claim 1, wherein the first and second collimators are Soller collimators.

25. The x-ray scanning system of claim 24, wherein the first collimator has an acceptance angle of less than approximately 0.2 degrees.

26. The x-ray scanning system of claim 3, wherein the detector assembly is fixed to select a particular diffraction angle range.

27. The x-ray scanning system of claim 26, wherein the diffraction angle range is approximately 2 to 3 degrees relative to the generated x-ray axis.

28. The x-ray scanning system of claim 14, wherein the conversion layer comprises CZT.

29. The x-ray scanning system of claim 28, further comprising a cooling system coupled to the flat panel detector, and wherein the cooling system is operable to cool the flat panel detector down to approximately minus 70 degrees C.

30. The x-ray scanning system of claim 1, further comprising a cooling system coupled to the flat panel detector, and wherein the cooling system is operable to cool the flat panel detector to a temperature, the temperature being in the approximate range of minus 30 degrees C. to minus 100 degrees C.

31. An x-ray scanning system, comprising:
a conveyor;
an x-ray source configured to generate x-rays toward the conveyor; and
a flat panel detector to receive diffracted x-rays from a container moving on the conveyor through the x-rays, wherein the flat panel detector is movable to select a particular diffraction angle of photons emitted from inside a bag for receipt by the flat panel detector.

32. The x-ray scanning system of claim 31, wherein the detector assembly further comprises the second collimator.

33. The x-ray scanning system of claim 31, wherein the detector assembly is movable to select a diffraction angle of up to approximately 4 degrees.

34. A method of container screening, comprising:
providing a flat panel detector having a photoconductor x-ray conversion layer; and
screening for a particular substance in a container at a transportation center using the flat panel detector to receive x-rays diffracted from the substance from an x-ray sheet beam incident upon the substance.

35. The method of claim 34, wherein the conversion layer comprises a scintillator layer.

36. The method of claim 34, wherein the conversion layer is amorphous.

37. The method of claim 34, wherein screening comprises performing a single pass x-ray diffraction scan of the container.

38. The method of claim 37, wherein screening further comprises performing a three-dimensional x-ray diffraction scan of the container in the single pass.

39. The method of claim 36, wherein the conversion layer comprises a polycrystalline material.

40. The method of claim 34, wherein the flat panel detector is operated at room temperature during the screening.

41. The method of claim 34, wherein screening comprises:
generating an x-ray sheet beam;
directing the x-ray sheet beam through the container;
generating diffracted x-rays from the x-ray sheet beam, the diffracted x-rays having a plurality of diffraction angles.

42. The method of claim 41, wherein screening further comprises performing an energy dispersive scan of the container to acquire a diffraction spectrum.

43. The method of claim 42, wherein performing the energy dispersive scan comprises selecting photons from the diffracted x-rays having a particular diffraction angle for detection by the flat panel detector.

44. The method of claim 42, wherein performing the energy dispersive scan further comprises counting single photons selected from the diffracted x-rays as the photons are intercepted by individual pixels in an array of pixels of the flat panel detector.

45. The method of claim 43, wherein the photons are selected using a collimator having an acceptance angle of approximately 2 degrees.

46. The method of claim 41, wherein generating an x-ray sheet beam further comprises generating tungsten k-alpha radiation.

47. The method of claim 41, wherein the flat panel detector comprises a two dimensional array of pixels and wherein screening comprises spatially locating a source of the diffracted x-rays.

48. The method of claim 47, wherein spatially locating comprises mapping a cross-section of the container defined by the x-ray sheet beam onto the array of pixels.

49. The method of claim 48, wherein the cross-section of the container defined by the x-ray sheet beam in the direction of the beam is compressed when mapped onto the array of pixels.

50. The method of claim 48, wherein spatially locating further comprising mapping a plurality of the cross-sections of the container to generate a three-dimensional x-ray diffraction scan of the container in a single pass.

51. The method of claim 34, wherein screening comprises performing a wavelength dispersive diffraction scan of the container.

52. The method of claim 34, wherein the conversion layer is crystalline.

53. The method of claim 52, wherein the conversion layer comprises CZT.

54. An x-ray scanning system, comprising:
a two dimensional amorphous flat panel detector array;
means for detecting a particular substance in a container at a transportation center using the two dimensional amorphous flat panel detector array to receive x-rays diffracted from the substance; and
means for cooling the flat panel detector down to between below room temperature and approximately minus 70 degrees C.

55. The x-ray scanning system of claim 54, wherein the means for detecting comprises means for generating an x-ray sheet beam.

56. The x-rays scanning system of claim 55, wherein the means for detecting further comprises:
means for directing the x-ray sheet beam through the container;
means for generating diffracted x-rays from the x-ray sheet beam, the diffracted x-rays having a plurality of diffraction angles; and
means for selecting diffracted x-rays to have a diffraction angle in a particular range.

57. An x-ray scanning system, comprising:
a conveyor;
an x-ray source configured to generate x-rays toward the conveyor, wherein the x-ray source generates an x-ray sheet beam; and
a detector to receive diffracted x-rays from a container moving on the conveyor through the x-rays.

58. The x-ray scanning system of claim 57, wherein the x-ray sheet beam comprises a plurality of parallel collimated beams.

59. The x-ray scanning system of claim 58, wherein the x-ray source comprises a target that generates radiation in the range of 30 to 120 KeV.

60. The x-ray scanning system of claim 59, wherein the target comprises tungsten.

61. The x-ray scanning system of claim 57, wherein the x-ray sheet beam has a width approximately in the range of 2 mm to 2 meters.

* * * * *